(12) United States Patent
Cheng et al.

(10) Patent No.: US 10,478,488 B2
(45) Date of Patent: Nov. 19, 2019

(54) LIPOSOMAL FLU VACCINE FORMULATION

(71) Applicants: Southwest Research Institute, San Antonio, TX (US); The Ohio State University, Columbus, OH (US)

(72) Inventors: Xingguo Cheng, San Antonio, TX (US); Kenneth H. Carson, San Antonio, TX (US); Joseph A. McDonough, Helotes, TX (US); Renukaradhya J. Gourapura, Wooster, OH (US); Chang Won Lee, Wooster, OH (US); Santosh Dhakal, Wooster, OH (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 15/723,793

(22) Filed: Oct. 3, 2017

(65) Prior Publication Data
US 2019/0099482 A1    Apr. 4, 2019

(51) Int. Cl.
A61K 39/12 (2006.01)
A61K 39/145 (2006.01)
A61K 39/00 (2006.01)

(52) U.S. Cl.
CPC ............ *A61K 39/145* (2013.01); *A61K 39/12* (2013.01); *A61K 2039/55511* (2013.01); *A61K 2039/55555* (2013.01); *C12N 2760/16134* (2013.01)

(58) Field of Classification Search
None
See application file for complete search history.

(56) References Cited

U.S. PATENT DOCUMENTS

| | | |
|---|---|---|
| 2015/0328305 A1 | 11/2015 | Smith et al. |
| 2017/0044215 A1 | 2/2017 | Zhang et al. |
| 2017/0114103 A9 | 4/2017 | Garcia-Sastre et al. |

OTHER PUBLICATIONS

Taus, F., et al: "Monosodium Urate Crystals Promote Innate Anti-Mycobacterial Immunity and Improve BCG Efficacy as a Vaccine Against Tuberculosis"; Published PLOS ONE, May 29, 2015 (11 pgs); <<http://journals.plos.org/plosone/article?id=10.1371/journal.pone.0127279>> (accessed Jun. 9, 2017).

*Primary Examiner* — Michelle S Horning
(74) *Attorney, Agent, or Firm* — Grossman, Tucker, Perreault & Pfleger, PLLC

(57) ABSTRACT

The present invention relates to the field of pharmaceutical and vaccine formulations. More specifically, formulations which comprise an antigen comprising a mixture of oligopeptides loaded into liposome nanoparticles, optionally including an adjuvant, to provide an improved immune response.

19 Claims, 23 Drawing Sheets
Specification includes a Sequence Listing.

Fig. 5

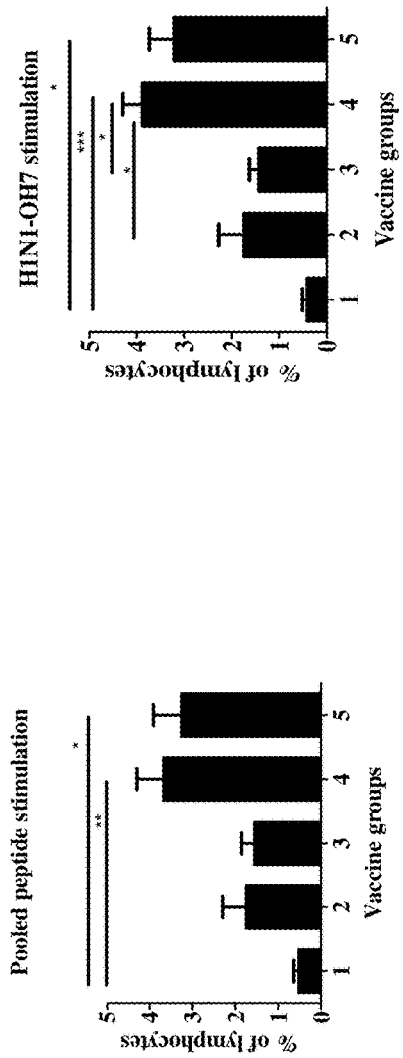
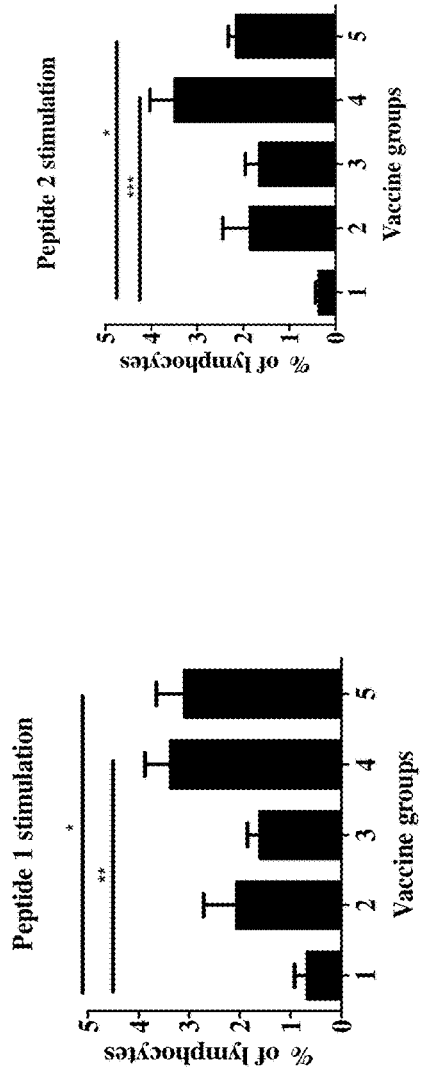
Fig. 10A
Fig. 10B
Fig. 10C
Fig. 10D

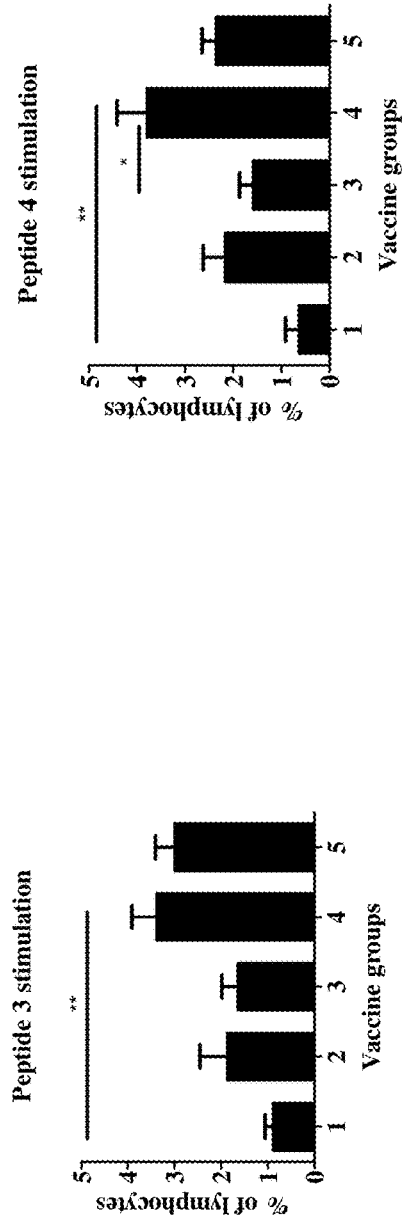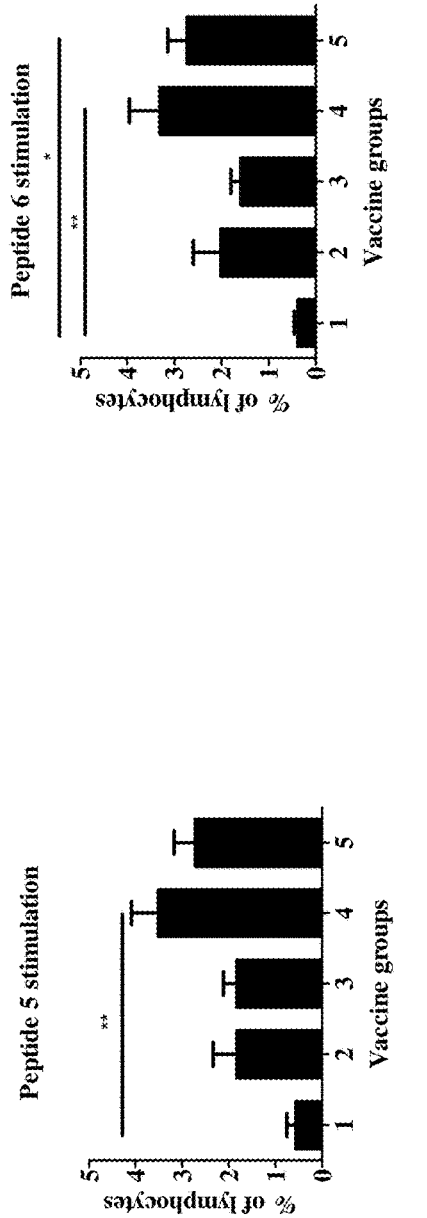
Fig. 10E
Fig. 10F
Fig. 10G
Fig. 10H

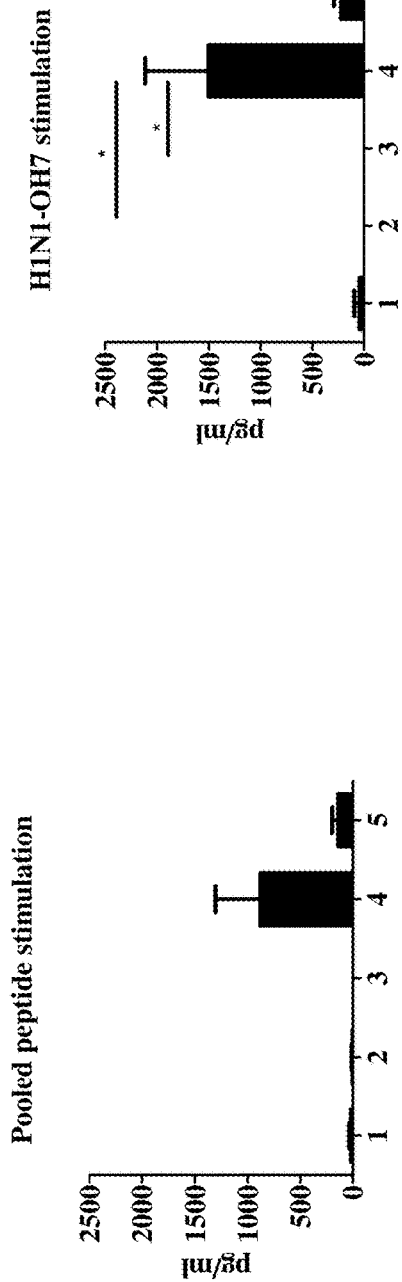
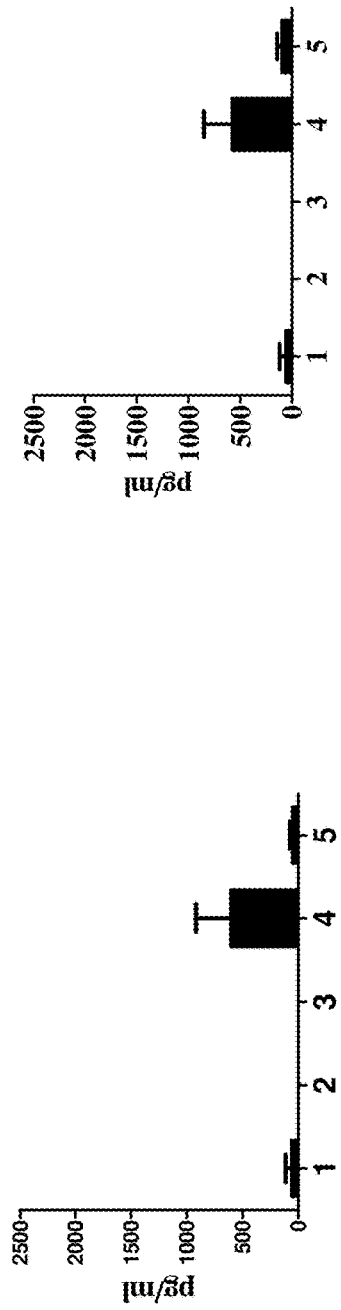
Fig. 12A
Fig. 12B
Fig. 12C
Fig. 12D

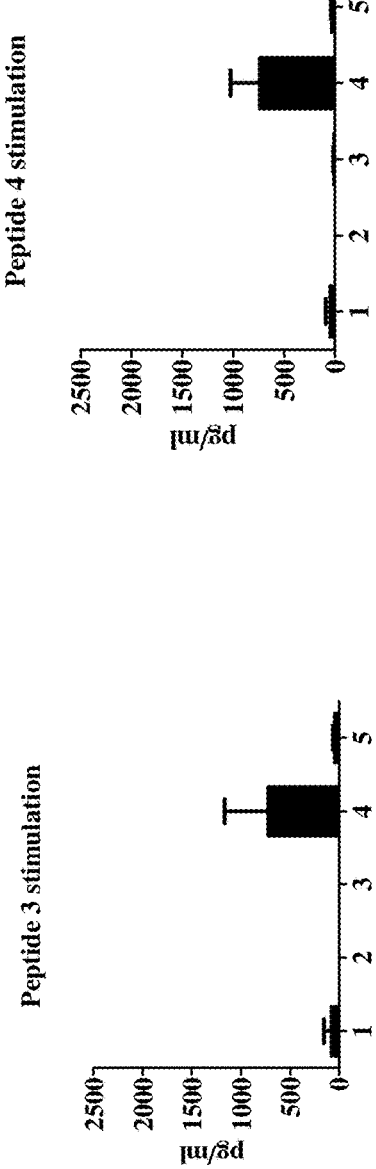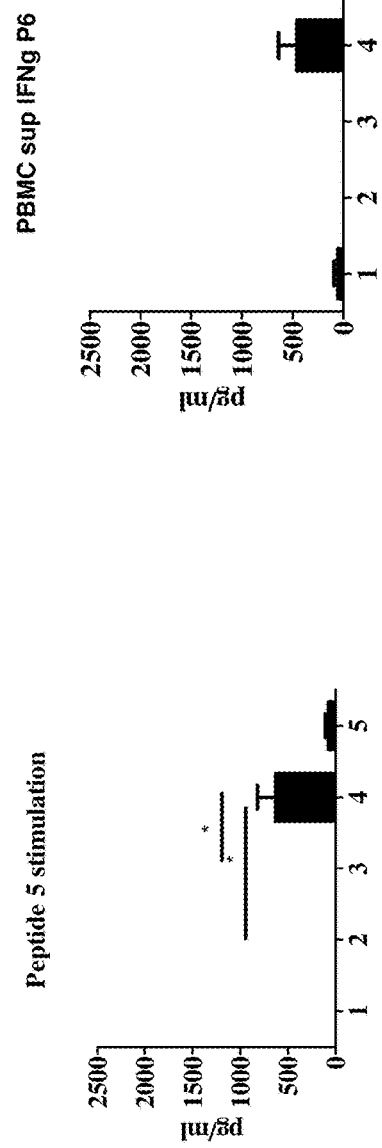
Fig. 12E
Fig. 12F
Fig. 12G
Fig. 12H

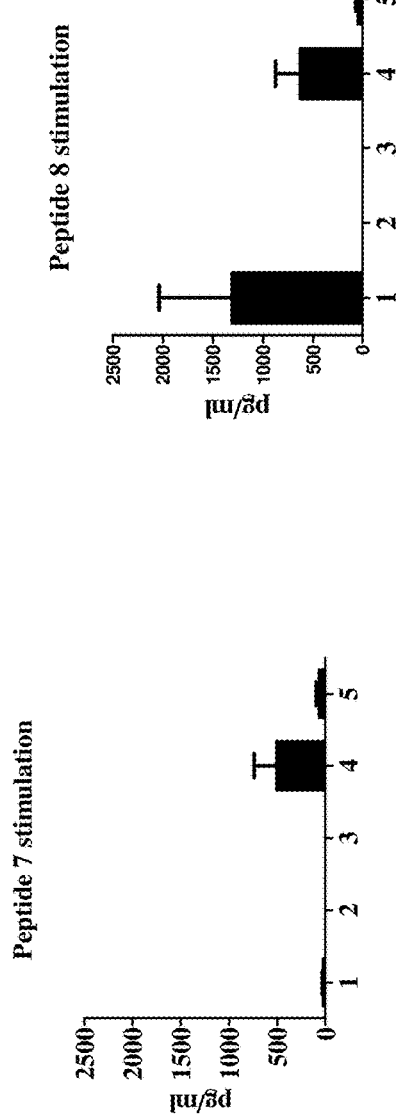
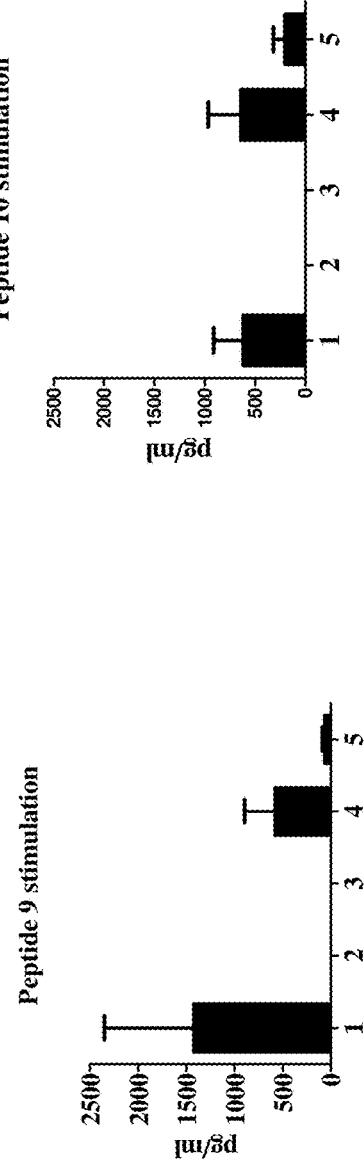
Fig. 12I
Fig. 12J
Fig. 12K
Fig. 12L

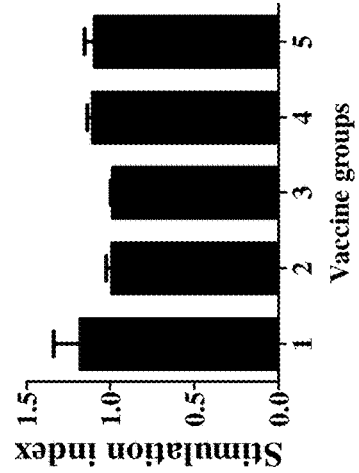
Fig. 13A
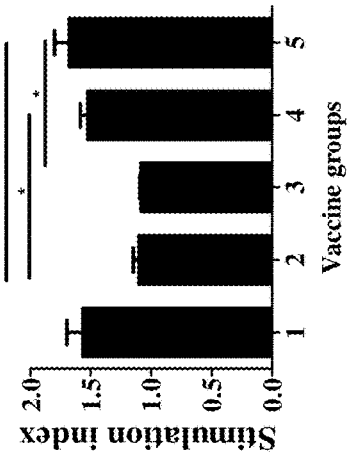
Fig. 13B
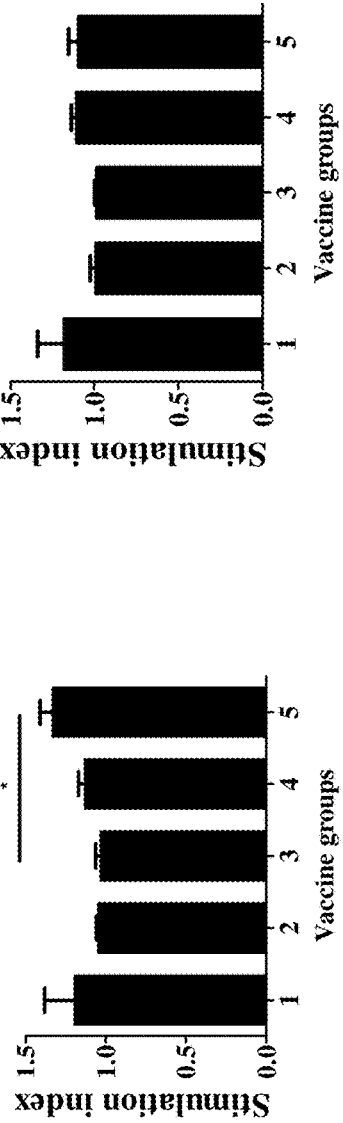
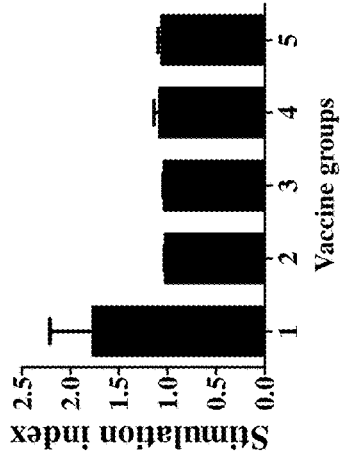
Fig. 13C
Fig. 13D

SEQUENCE LISTING

<160> NUMBER OF SEQ ID NOS: 10

<210> SEQ ID NO 1
<211> LENGTH: 23

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Leu Leu Thr Glu Val Glu Thr Pro Ile Arg Asn Gly Trp Glu Cys
1               5                   10                  15

Lys Cys Asn Asp Ser Ser Asp
            20

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asn Ser Glu Asn Gly Thr Cys Tyr Pro Gly Asp Phe Ile Asp Tyr Glu
1               5                   10                  15

Glu Leu Arg Glu Gln Leu Ser Ser Val Ser Ser Phe Glu Lys Phe Glu
            20                  25                  30

Ile Phe

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asn Pro Glu Asn Gly Thr Cys Tyr Pro Gly Tyr Phe Ala Asp Tyr Glu
1               5                   10                  15

Glu Leu Arg Glu Gln Leu Ser Ser Val Ser Ser Phe Glu Arg Phe Glu
            20                  25                  30

Ile Phe

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Glu Leu Lys His Leu Leu Ser Arg Ile Asn His Phe Glu Lys Ile
1               5                   10                  15

Gln Ile Ile Pro Lys Ser Ser Trp Ser Ser His Glu Ala Ser Leu Gly
            20                  25                  30

Val Ser Ser
        35

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 5

Ser Ser Asp Asn Gly Thr Cys Tyr Pro Gly Asp Phe Ile Asp Tyr Glu
1               5                   10                  15

Glu Leu Arg Glu Gln Leu Ser Ser Val Ser Ser Phe Glu Arg Phe Glu
            20                  25                  30

Ile Phe

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Thr Glu Leu Lys Leu Ser Asp Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Met Ala Arg Leu Gly Lys Gly Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ser Asp Gly Gly Pro Asn Leu Tyr
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Ser Asp Thr Val Gly Trp Ser Trp
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 10

Ala Thr Glu Tyr Ile Met Lys Gly Val Tyr
1               5                   10
```

LIPOSOMAL FLU VACCINE FORMULATION

SEQUENCE LISTING

The instant application contains a Sequence Listing which has been submitted electronically in ASCII format and is hereby incorporated by reference in its entirety. Said ASCII copy, created on Sep. 29, 2017, is named SwRI3928_SL.txt and is 3,480 bytes in size.

FIELD

The present invention relates to the field of pharmaceutical and vaccine formulations. More specifically, formulations which comprise an antigen comprising a mixture of oligopeptides loaded into liposome nanoparticles, optionally including an adjuvant, to provide an improved immune response.

BACKGROUND

Vaccination is one of the most effective tools for mitigating the impact of influenza epidemics and pandemics. However, commercially available flu vaccines are in general directed specifically towards a specific strain contained in the vaccine. Current flu vaccine strategies have typically demonstrated a lack of cross-protective immunity (i.e., the vaccine is not effective against multiple strains or types of flu virus). For example, authorities from many countries collaborate with one another to predict the strain of influenza A virus that is likely to cause flu in the upcoming months. While these types of vaccination programs can work to contain a seasonal flu, they become less effective when the flu epidemic is caused by a different influenza A strain than was predicted. In addition, there is often a lack of long-term effectiveness (i.e., the vaccine protection is short lived and not sufficiently potent).

SUMMARY

An immunogenic composition comprising:
SEQ ID NO: 1 or an oligopeptide having 90% or more amino acid sequence identity to SEQ ID NO: 1;
SEQ ID NO: 2 or an oligopeptide having 90% or more amino acid sequence identity to SEQ ID NO: 2;
SEQ ID NO: 3 or an oligopeptide having 90% or more amino acid sequence identity to SEQ ID NO: 3;
SEQ ID NO: 4 or an oligopeptide having 90% or more amino acid sequence identity to SEQ ID NO: 4;
SEQ ID NO: 5 or an oligopeptide having 90% or more amino acid sequence identity to SEQ ID NO: 5;
SEQ ID NO: 6 or an oligopeptide having 90% or more amino acid sequence identity to SEQ ID NO: 6;
SEQ ID NO: 7 or an oligopeptide having 90% or more amino acid sequence identity to SEQ ID NO: 7;
SEQ ID NO: 8 or an oligopeptide having 90% or more amino acid sequence identity to SEQ ID NO: 8;
SEQ ID NO: 9 or an oligopeptide having 90% or more amino acid sequence identity to SEQ ID NO: 9; and
SEQ ID NO: 10 or an oligopeptide having 90% or more amino acid sequence identity to SEQ ID NO: 10.
The above oligopeptide mixture is combined into a liposomal nanoparticle optionally in the presence of an adjuvant and one or more appropriate excipients to serve as a medicament or vaccine composition against influenza.

In method form, the present invention relates to a method for eliciting an immune response and conferring protection against influenza virus in a subject, wherein the method comprises administering to the subject a vaccine comprising:
SEQ ID NO: 1 or an oligopeptide having 90% or more amino acid sequence identity to SEQ ID NO: 1;
SEQ ID NO: 2 or an oligopeptide having 90% or more amino acid sequence identity to SEQ ID NO: 2;
SEQ ID NO: 3 or an oligopeptide having 90% or more amino acid sequence identity to SEQ ID NO: 3;
SEQ ID NO: 4 or an oligopeptide having 90% or more amino acid sequence identity to SEQ ID NO: 4;
SEQ ID NO: 5 or an oligopeptide having 90% or more amino acid sequence identity to SEQ ID NO: 5;
SEQ ID NO: 6 or an oligopeptide having 90% or more amino acid sequence identity to SEQ ID NO: 6;
SEQ ID NO: 7 or an oligopeptide having 90% or more amino acid sequence identity to SEQ ID NO: 7;
SEQ ID NO: 8 or an oligopeptide having 90% or more amino acid sequence identity to SEQ ID NO: 8;
SEQ ID NO: 9 or an oligopeptide having 90% or more amino acid sequence identity to SEQ ID NO: 9; and
SEQ ID NO: 10 or an oligopeptide having 90% or more amino acid sequence identity to SEQ ID NO: 10; to elicit an immune response and confer protection against influenza virus. As noted above, in method form, the oligopeptide mixture may again be combined into a liposomal nanoparticle optionally in the presence of an adjuvant and one or more appropriate excipients.

BRIEF DESCRIPTION OF THE DRAWINGS

Figure 5:
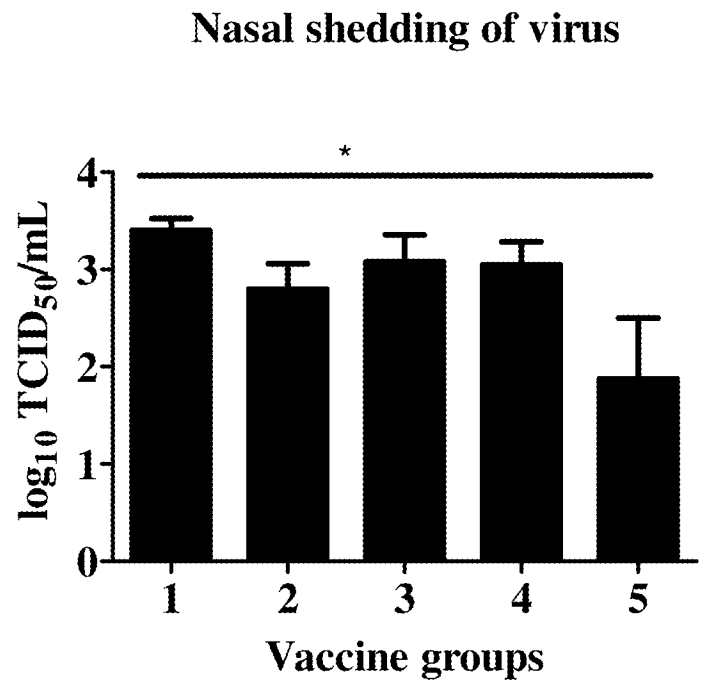

FIG. 5 evaluates virus shedding detection in nasal swab samples for Groups 1-5 of Table 5.

FIGS. 10A, 10B, 10C, 10D, 10E, 10F, 10G, 10H, 10I, 10J, 10K and 10L illustrate that virus and peptides epitopes specific T-helper/memory ($CD3^+CD4^+CD8\alpha^+$) cells in peripheral blood mononuclear cells (PBMCs) were significantly increased in the liposome vaccine formulations (after restimulation with peptides and virus) out of Groups 1-5 of Table 5.

FIGS. 12A, 12B, 12C, 12D, 12E, 12F, 12G, 12H, 12I, 12J, 12K and 12L illustrate the IFNγ recall response in PBMCs at DPC6 restimulated with pooled peptides, H1N1-OH7 virus and each of the individual oligopeptides separately.

FIGS. 13A, 13B, 13C and 13D illustrate the high proliferative response of mononuclear cells in blood and TBLN after pooled peptides and H1N1-OH7 virus stimulation in liposome vaccine groups out of groups 1-5 of Table 5.

DETAILED DESCRIPTION

Figure 1A:
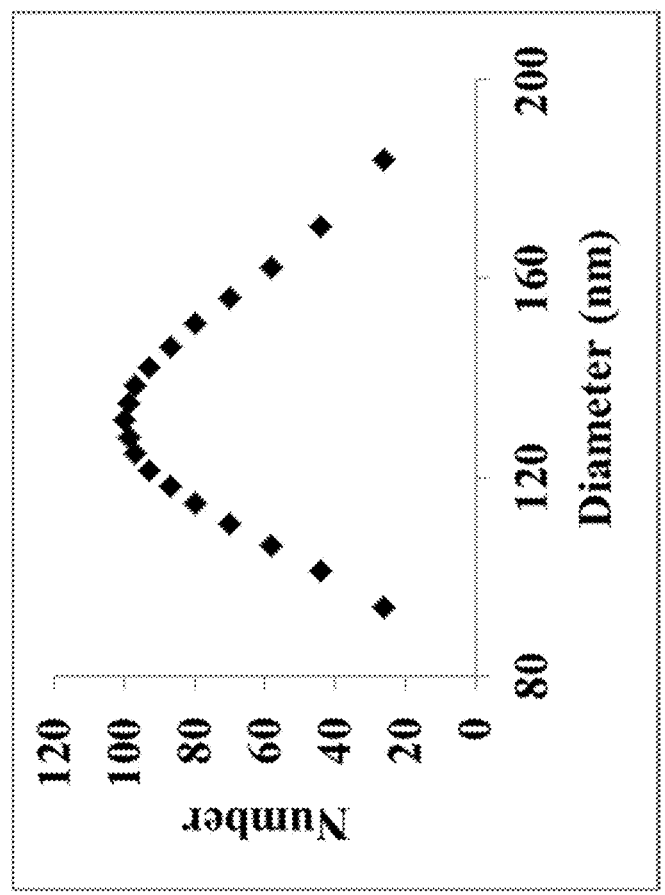
FIGS. 1A and 1B shows the size distribution of liposome nanoparticles and polarized optical microscopy image of the MSU crystal adjuvants respectively.

The present invention relates to formulations which comprise, consist essentially of, or consist of an antigen (mixture of oligopeptides) preferably with an adjuvant and preferably loaded into liposome nanoparticles. A peptide is reference to amino acid residue, connected to one another typically by peptide bonds between alpha-amino and carbonyl groups of adjacent amino acids. The oligopeptides herein preferably contain between 9-35 amino acids in length. Such formulations provide a cross-protective immune response against the influenza virus.

As used herein in the context of immunization, immune response and vaccination, the term "adjuvant" refers to any substance when used in combination with the adjuvant produces a more robust immune response than the antigen alone.

The percent amino acid sequence identity of a first oligopeptide sequence to a second oligopeptide sequence, as referred to in the context of the present invention, is defined as the number of amino acid residues in the second sequence that match in both position and identity to those in the first sequence, divided by the total number of amino acid residues in the second oligopeptide (where both first and second polypeptides have the same number of amino acid residues) and multiplied by 100. In the present invention, it is preferred that the oligopeptide sequence identity in the defined sequences is 90% or more, 91% or more, 92% or more, 93% or more, 94% or more, 95% or more, 96% or more, 97% or more, 98% or more, 99% or more, or 100%.

The amino acid abbreviations in the present context have the following meanings shown in Table 1:

TABLE 1

| Amino Acid Abbreviations | |
|---|---|
| Amino Acid | Symbol |
| Alanine | A |
| Arginine | R |
| Asparagine | N |
| Aspartic Acid | D |
| Cysteine | C |
| Glutamine | Q |
| Glutamic Acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Theonine | T |
| Tryptophan | W |
| Tyrosine | Y |
| Valine | V |

Preferably, the antigen herein comprises a mixture of ten (10) oligopeptides having the sequence identification number (SEQ ID NO:) identified in Table 2 below, entitled "Flu Oligopeptides."

TABLE 2

| Flu Oligopeptides | | | | |
|---|---|---|---|---|
| Label | Peptide | No. of Amino Acids | Charge | Nature |
| SEQ ID NO: 1 | SLLTEVETPIRNGWECKCNDSSD | 23 | -3 | Acidic |
| SEQ ID NO: 2 | NSENGTCYPGDFIDYEELREQLSSVSSFEKFEIF | 34 | -6 | Acidic |
| SEQ ID NO: 3 | NPENGTCYPGYFADYEELREQLSSVSSFERFEIF | 34 | -5 | Acidic Hydrophobic |
| SEQ ID NO: 4 | EELKHLLSRINHFEKIQIIPKSSWSSHEASLGVSS | 35 | 3 | Basic |
| SEQ ID NO: 5 | SSDNGTCYPGDFIDYEELREQLSSVSSFERFEIF | 34 | -6 | Acidic, Hydrophobic |
| SEQ ID NO: 6 | CTELKLSDY | 9 | -1 | Acidic |
| SEQ ID NO: 7 | KMARLGKGY | 9 | -3 | Basic |
| SEQ ID NO: 8 | VSDGGPNLY | 9 | -1 | Acidic |

TABLE 2-continued

Flu Oligopeptides

| Label | Peptide | No. of Amino Acids | Charge | Nature |
|---|---|---|---|---|
| SEQ ID NO: 9 | NSDTVGWSW | 9 | −1 | Acidic |
| SEQ ID NO: 10 | ATEYIMKGVY | 10 | 0 | Neutral, Hydrophobic |

The method of producing the above referenced oligopeptides is not limited, and typically comprises joining two or more amino acids to form the oligopeptide. The oligopeptide may, however, be prepared by direct chemical synthesis (e.g. incorporating one amino acid at a time until the full oligopeptide is formed) or by recombinant methods. Such general methods are well known to the skilled person and may be adapted to the present invention as desired. In some instances, the oligopeptides of the present invention may comprise additional amino acid sequences at one or both termini to help in synthesis of the oligopeptide.

As can now be appreciated, the antigen herein preferably comprises a mixture of the above ten oligopeptides and their corresponding oligopeptides with the requisite sequence identify. Preferably, the ten oligopeptides are present in substantially equal concentration by weight in the liposome nanoparticle, such that the concentration by weight as between the oligopeptides may vary +/−5.0%, +/−4.0%, +/−3.0%, +/−2.0%, +/−1.0%, or no variation.

Figure 1B:
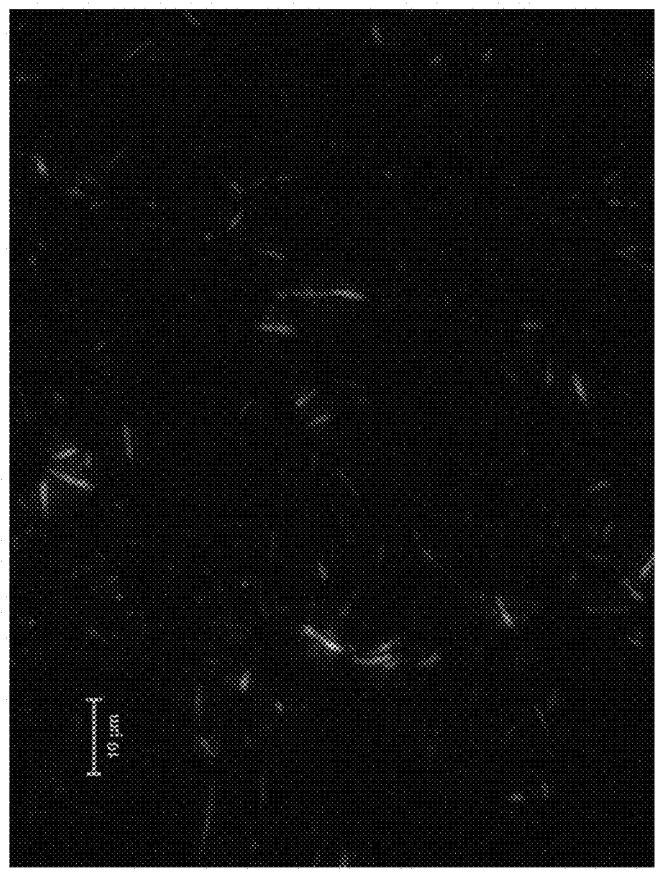

The antigen herein is preferably administered in combination with an adjuvant. As noted, the adjuvant for administration in combination with the antigen enhances and/or boosts the immune response. Adjuvants herein include CpG oligodeoxynucleotide, Imiquimod, Alum (aluminum hydroxide/magnesium hydroxide) and MF59 (an oil-in-water emulsion of squalene oil). One particularly preferred adjuvant herein is selected from mono sodium urate (MSU) crystals (FIG. 1B), $C_5H_3N_4O_3Na$:

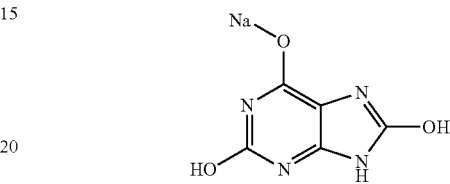

The adjuvant herein is preferably mixed with the liposome nanoparticles which are loaded with the mixture of oligopeptides, at a level of 1.0 mg to 10.0 mg per dose. More preferably, the adjuvant is present at a level of 4.0 mg to 7.0 mg per dose, and in a most preferred embodiment, the adjuvant is present at a level of 4.5 mg to 5.5 mg per dose.

The liposome nanoparticle carrier herein having a lipid bilayer is employed as the preferred vehicle for antigen administration. Such liposome nanoparticle preferably has a diameter in the range of 50 nm to 200 nm (FIG. 1A), more preferably 100 nm to 200 nm, and even more preferably, a diameter of 150 nm to 200 nm. In a particularly preferred embodiment, the liposome nanoparticle has a diameter in the range of 160 nm to 180 nm. In addition, the liposome nanoparticle herein is further characterized as preferably having a Zeta potential in the range of −15.0 to −25.0 mV, more preferably in the range of −18.0 mV to −23.0 mV.

Liposome Particle Preparations

The oligopeptides were freeze-dried to remove $H_2O$. Depending on peptide nature (i.e., acidic, basic, or neutral), various methods were used to solubilize each peptide at maximum concentrations. See Table 3 below for methods used to solubilize the oligopeptides:

TABLE 3

| Peptide (each with 15 mg) | Method | pH adjustment | Adjust final volume to ___ mL with $H_2O$ | Final concentration [mg/mL] |
|---|---|---|---|---|
| 1 Acidic | 50 µL NH4OH (10%) + 400 µL H2O | Adjust to pH 7.5 with Acetic acid (10%) | 0.600 | 25.0 |
| 2 Acidic | 50 µL NH4OH (10%) + 400 µL H2O | Adjust to pH 7.5 with Acetic acid (10%) | 0.600 | 25.0 |
| 6 Acidic | 50 µL NH4OH (10%) + 400 µL H2O | Adjust to pH 7.5 with Acetic acid (10%) | 0.600 | 25.0 |
| 8 Acidic | 50 µL NH4OH (10%) + 400 µL H2O. | Adjust to pH 7.5 with Acetic acid (10%) | 0.600 | 25.0 |
| 9 Acidic | 50 µL NH4OH (10%) + 400 µL H2O | Adjust to pH 7.5 with Acetic acid (10%) | 0.600 | 25.0 |
| 3 Acidic, Hydrophobic | 100 µL NH4OH (10%) + 1000 µL (1 mL) of 8M Urea | Adjust to pH 7.5 with Acetic acid (10%) | 1.380 | 10.9 |
| 5 Acidic, Hydrophobic | 100 µL NH4OH (10%) + 1000 µL (1 mL) of 8M Urea. | Adjust to pH 7.5 with Acetic acid (10%) | 1.380 | 10.9 |

TABLE 3-continued

| Peptide (each with 15 mg) | Method | pH adjustment | Adjust final volume to ___ mL with H₂O | Final concentration [mg/mL] |
|---|---|---|---|---|
| 4 Basic | 50 μL CH3COOH (10%) + 300 μL H2O | Adjust to pH 6 with NH4OH (10%) | 0.450 | 33.3 |
| 7 Basic | 50 μL CH3COOH (10%) + 300 μL H2O | Adjust to pH 6 with NH4OH (10%) | 0.450 | 33.3 |
| 10 Neutral, Hydrophobic | 800 μL 8M Urea | pH not adjusted | 0.800 | 18.8 |

Similar methods were used for like groups. Once in solution, like peptides were combined and stored according to Table 4. For example, Group A contains all acidic peptides (1, 2, 6, 8, and 9) and each peptide concentration was 5 mg/mL at pH 7.5.

TABLE 4

Grouping of Oligopeptides

| Group | Peptides | Concentration [mg/mL] of combined oligopeptides (total) |
|---|---|---|
| Acidic (A) | 1, 2, 6, 8, 9 | 25.0 (5 mg each oligopeptide 1, 2, 6, 8, 9) |
| Acidic/Hydrophobic (A2) | 3, 5 | 10.9 (5.45 mg/mL each oligopeptide 3 and 5) |
| Basic (B) | 4, 7 | 33.3 (16.65 mg/mL each oligopeptide 4 and 7) |
| Neutral (N) | 10 | 18.8 (oligopeptide 10) |

A lipid cake is then formed by combining 1 gram soy lecithin, 125 mg cholesterol, and 24 μL alpha tocopherol in 25 mL MeOH/CHCl3 (1:1 ratio) to form a clear solution. The 25 mL lipid solution was aliquoted 5 mL each into a glass vial (40 mL). Each vial was rotary evaporated to form lipid cakes. Each vial was flushed with $N_2$ and dried in vacuum for 1.5 hr to remove any residual solvent. The 5 lipid cakes were labeled A, B, C, D, E. Each lipid cake will contain about 200 mg soy lecithin, 25 mg cholesterol, and 5 μL alpha tocopherol.

Formation of Liposome Control (No Peptide Drug)

Next lipid cake A was hydrated with 0.5 mL PBS, and additional 1.5 mL PBS to fully remove the cake from the glass vial wall. The suspension was subject to repeated freeze-thawed (liquid N2 for freeze, 40° C. ultrasonic water bath) five times. After that 7 mL PBS was added to the solution and it was extruded using an extruder for LIPEX simvastatin, passing 1 μm filter membrane 5 times, 0.4 μm filter membrane 8 times, and 0.2 μm filter membrane 10 times. The final volume was brought to 10.6 mL. This served as the liposome control (no oligopeptides).

Formation of Liposome Encapsulating 10 Oligopeptides

Lipid cake B hydrated with 0.4 mL of Group A-Acidic peptides (25 mg/mL total peptides, 5 peptides) by repeated vortex, then added 0.1 mL PBS, pH 7.4 (total 0.5 mL)

Lipid cake C hydrated with 0.367 mL of Group A2-Acidic/Hydrophobic peptides [10.9 mg/mL] by repeated vortex, then added 0.133 mL PBS, pH 7.4 (total 0.5 mL)

Lipid cake D hydrated with 0.12 mL of Group B-Basic peptides [33.3 mg/mL] by repeated vortex, then added 0.38 mL PBS, pH 7.4 (total 0.5 mL)

Lipid cake E hydrated with 0.106 mL of Group N-Neutral peptide [18.8 mg/mL] by repeated vortex, then added 0.394 mL PBS, pH 7.4 (total 0.5 mL)

Each of the above B, C, D, E lipid suspensions was briefly sonicated and then combined together. The whole suspension (2 mL) was subjected to a 5 times freeze-thaw cycle using liquid $N_2$ and a 40° C. sonication water bath. Afterwards, the lipid suspension diluted with 40.5 mL 1×PBS. The total combined B, C, D, E liposome (total 42.5 mL) were extruded through a 0.1 μm membrane to form a homogenous liposome which contained all 10 oligopeptides with each peptide loaded at 0.047 mg/mL (total peptide loading 0.47 mg/mL).

The amount of each oligopeptide in the mixture of ten oligopeptides loaded into the liposomal particle is therefore preferably in the range of 0.01 mg to 0.1 mg. Accordingly, the ten oligopeptides are in total preferably present in the liposomal particle herein at a level of 0.1 mg to 1.0 mg. The dosage for any one individual is not especially limited and may range from 1.0 μg to 1.0 g of the oligopeptide loaded liposome per individual, depending upon the size, weight and species of the individual involved.

The present invention is now described in further detail below in combination with the drawings and the specific embodiments. That is, liposome formulations as well as controls were evaluated in a pig model as summarized in Table 5 utilizing the mixture of ten oligopeptides identified in Table 2 to confirm their efficacy in the treatment of influenza virus. The pig vaccinations were performed using via intranasal delivery.

TABLE 5

Groups Utilized For Pig Flu Vaccination Study

| Group | Vaccine | Challenge |
|---|---|---|
| 1. Mock | PBS | H1N1-OH7 |
| 2. Peptides Only | Peptides | H1N1-OH7 |
| 3. Peptides + Adjuvant | Peptides + MSU | H1N1-OH7 |
| 4. Liposome Nanoparticles + Peptides | Liposome + Peptides | H1N1-OH7 |
| 5. Liposome Nanoparticles + Peptides + Adjuvant | Liposome + Peptides + MSU | H1N1-OH7 |

Pigs were monitored daily for flu symptoms (temperature, respiratory distress, cough, and reduced food intake) and body weight recorded and collection of clinical samples (nasal swabs) were performed at days post challenge (DPC) 0, 2, 4 and 6 for virus detection. Blood samples were collected from all the pigs before inoculation of the first vaccine dose, on the day of virus challenge, and at the time of euthanasia. On day 6 post-challenge all the pigs were euthanized and the lung pneumonic lesions were scored. The lung samples were collected for histopathology (H&E staining) and BAL fluid and plasma samples were used to determine the virus specific IgA and IgG antibody response by ELISA. Infectious virus titers in nasal swab and BAL fluid were determined by infecting MDCK cell culture monolayers. To determine the frequency of SIV epitope-specific T-helper/memory cell responses, isolated PBMCs and tracheobronchial lymph nodes (TBLN) mononuclear cells were cultured with medium only (control), SIV used for challenge (H1N1-OH7), 10 peptides together (pooled peptides) or individual peptides used in the vaccine preparation. Cells were immunostained using a combination of pig lymphocyte specific cell surface markers and the data were analyzed by flow cytometry. The induced mucosal and systemic antibody and T cell responses were evaluated.

Figure 2:
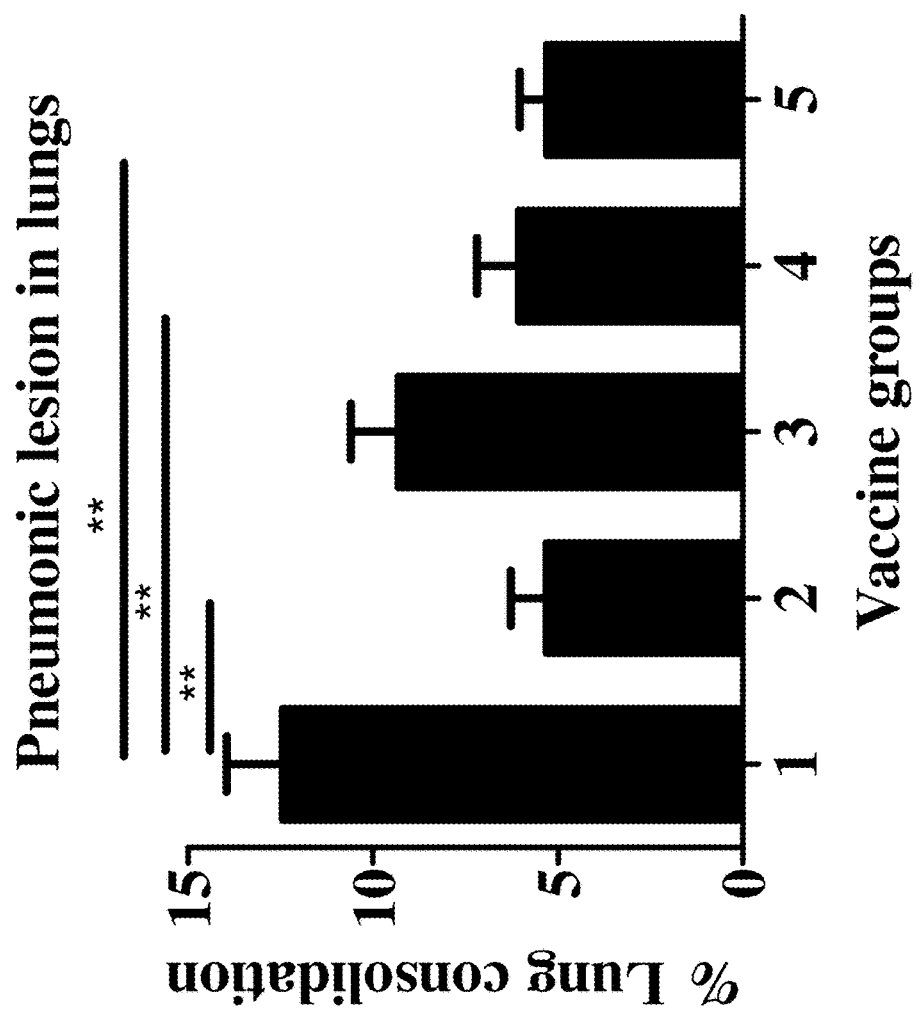
FIG. 2 illustrates the macroscopic pneumonic lesions in the lungs (% lung consolidation due to influenza infection) for Groups 1-5 of Table 5.
Figure 3:
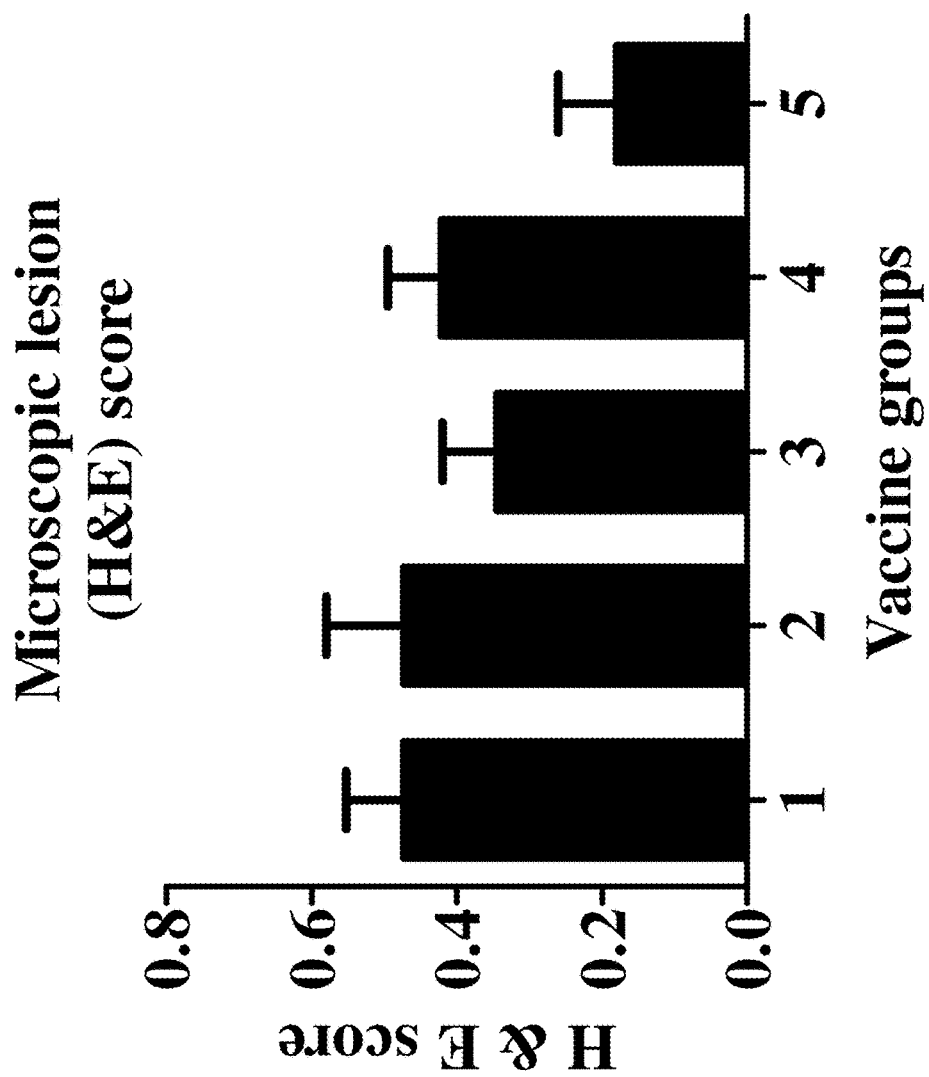
FIG. 3 shows the microscopic lesions in lungs (H&E score) due to influenza infection for Groups 1-5 of Table 5.

1. Liposomal Vaccine Results in a Lung Protective Effect:

As shown in FIG. 2 (pneumonic lesion in the lungs) and FIG. 3 (microscopic lesion (H&E) score, Group 5 (liposome-peptide nanoparticle with MSU adjuvant) resulted in relatively lower percentage of lung consolidation and lung lesions score than all the other groups.

Figure 4:
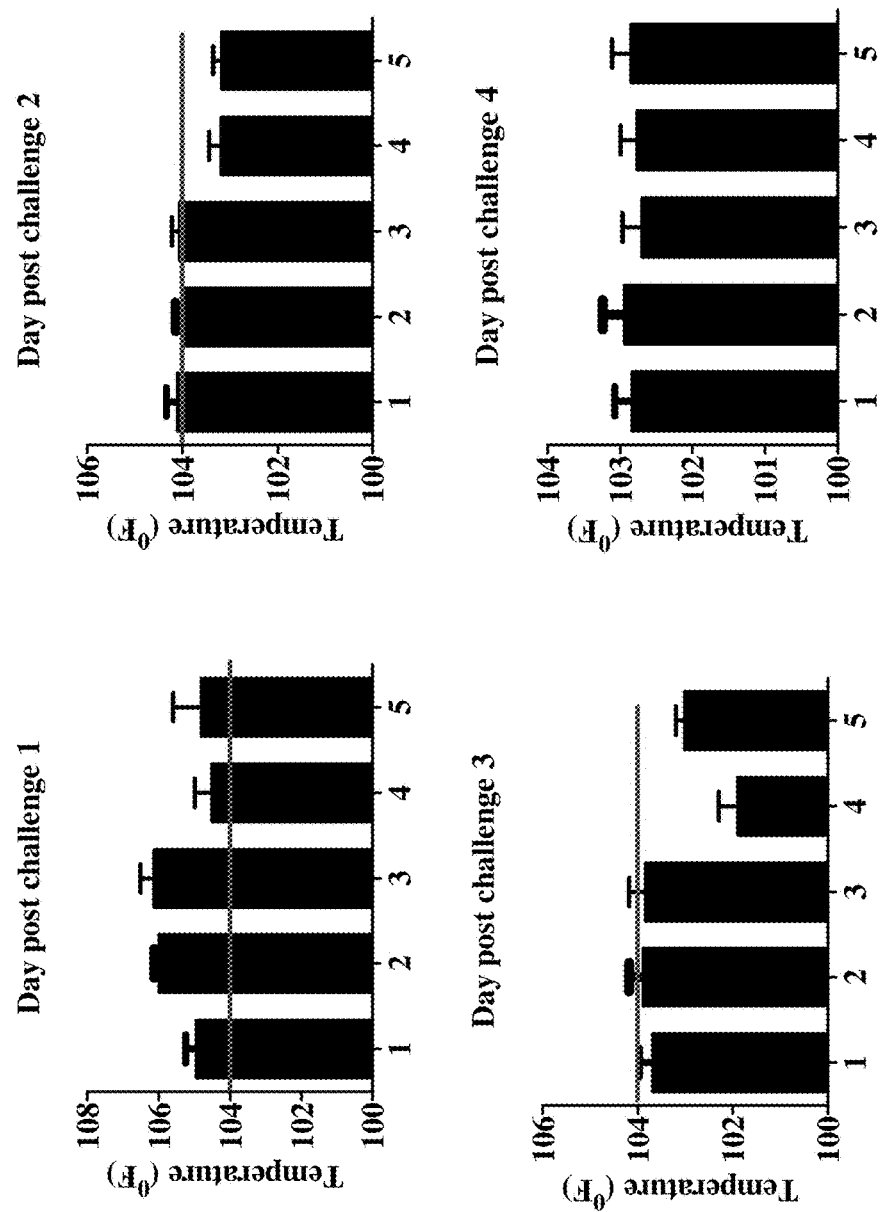
FIG. 4 identifies body temperature from days 1-4 post influenza infection (>104° F.).

2. Liposomal Vaccine (with and without Adjuvant) Protect Pigs from Fever:

As shown in FIG. 4, Group 4 (liposome+peptides) and Group 5 (liposome-peptide nanoparticle with MSU adjuvant) resulted in relatively lower body temperature after challenge with H1N1 flu virus on days 2 and 3. At day 4, all groups recovered from fever.

Figure 6:
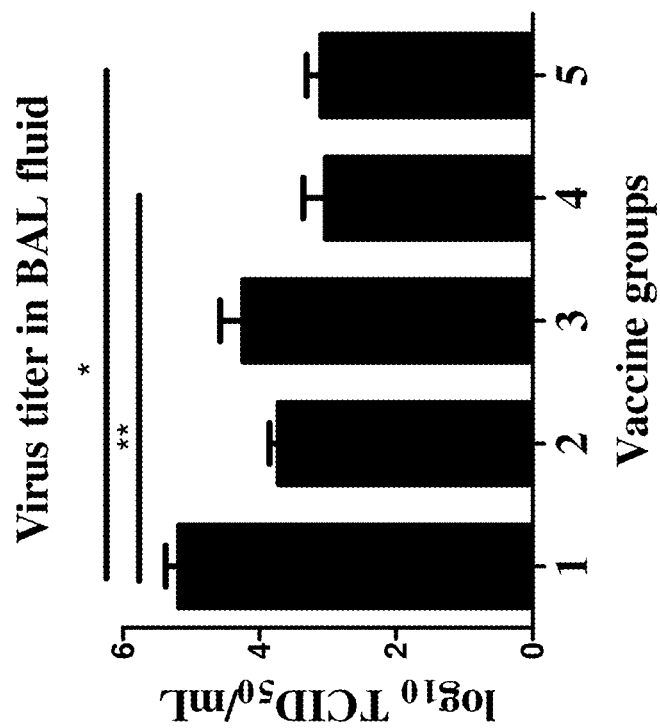
FIG. 6 evaluates the virus titer in BAL fluid for Groups 1-5 of Table 5.
Figure 7B:
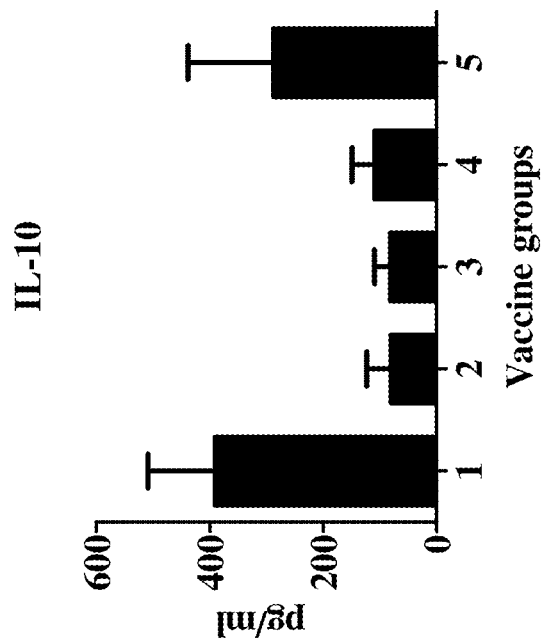
FIGS. 7A, 7B, 7C, and 7D evaluate the cytokine response in BAL fluid of vaccine delivered and influenza infected pigs for Groups 1-5 of Table 5.
Figure 7A:
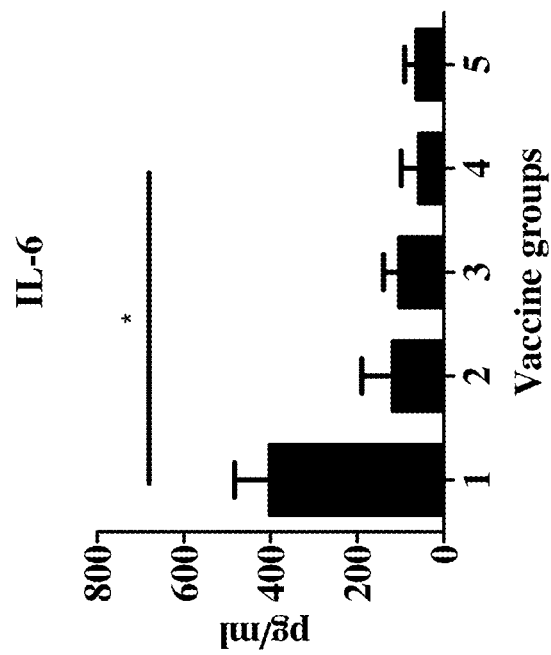
Figure 7D:
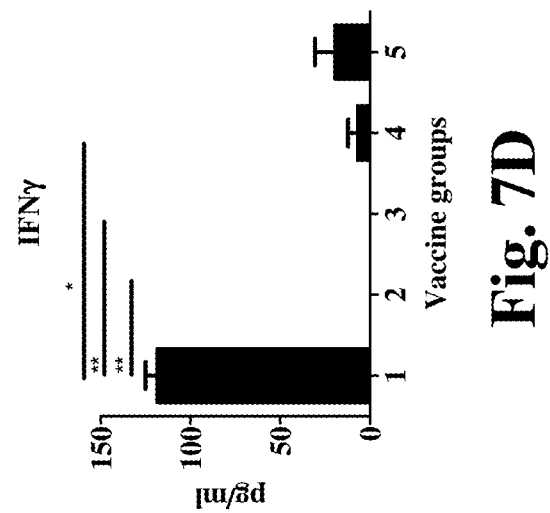
Figure 7C:
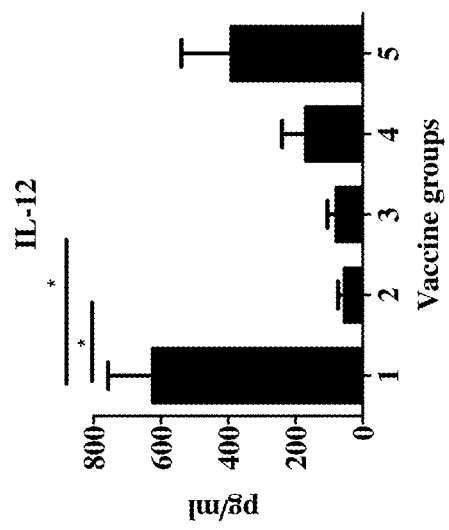
Figure 8C:
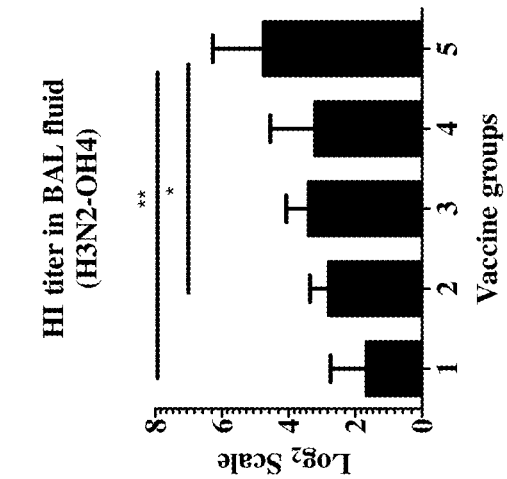
FIGS. 8A, 8B, 8C, 8D, 8E and 8F illustrate the hemagglutination inhibition (HI) antibody response in BAL fluid and plasma in the Groups 1-5 of Table 5.
Figure 8B:
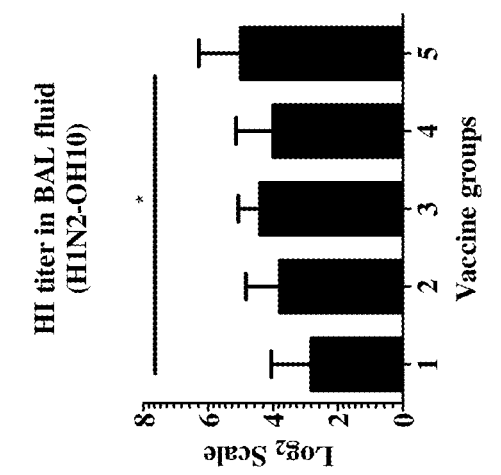
Figure 8A:
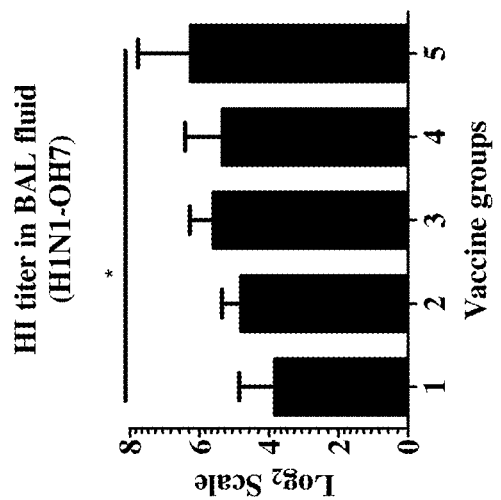
Figures 8D, 8E, 8F:
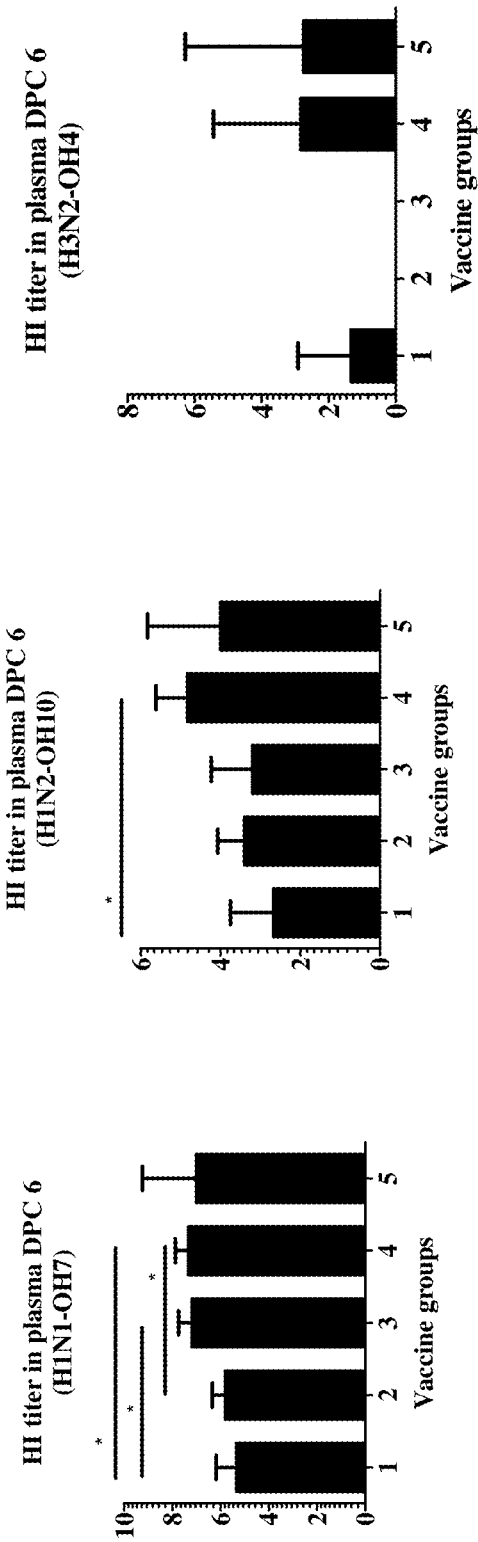
Figures 9A, 9B, 9C:
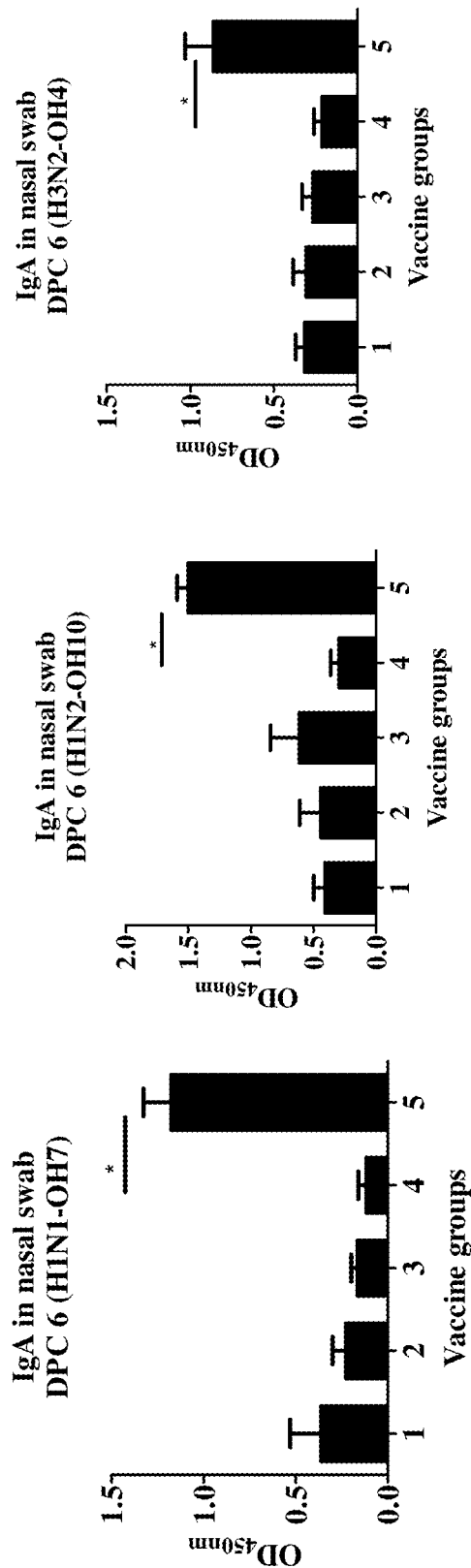
FIGS. 9A, 9B, 9C, 9D, 9E, 9F, 9G and 9H illustrate the IgA and IgG antibody response in nasal swab, BAL fluid and plasma at 6 Day post challenge (DPC6) in the groups 1-5 of Table 5.
Figure 9F:
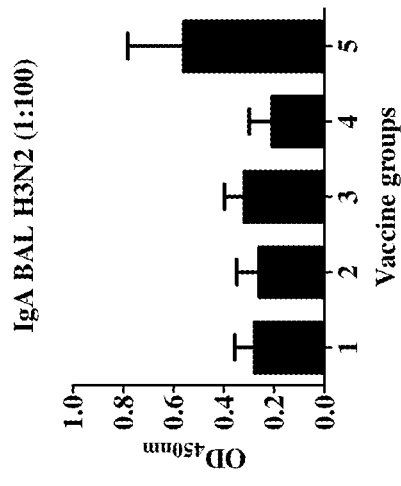
Figure 9E:
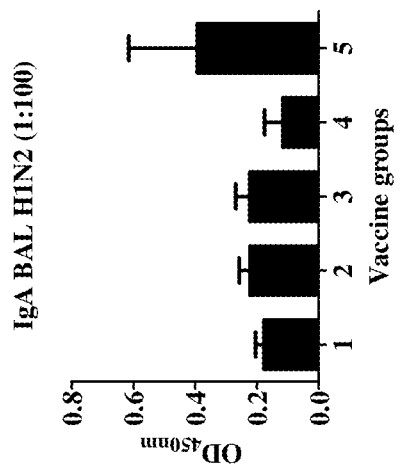
Figure 9D:
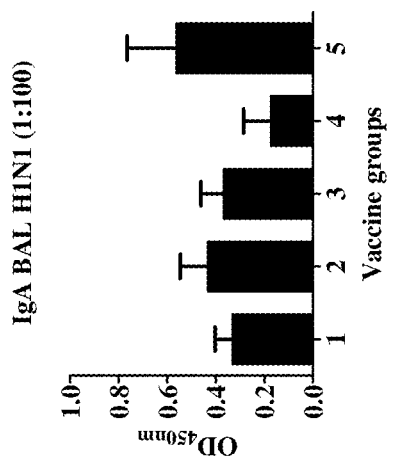
Figure 9H:
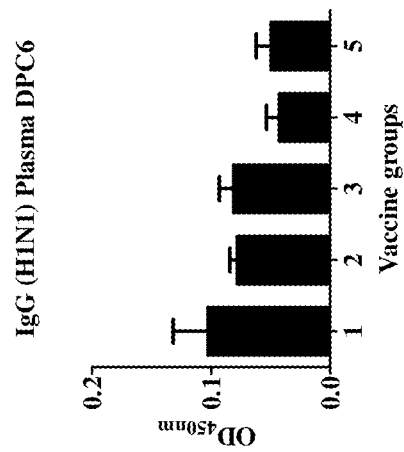
Figure 9G:
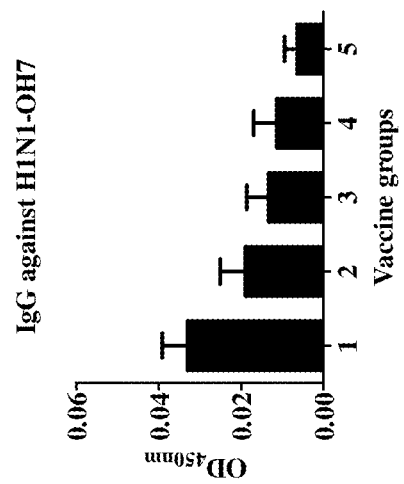
Figure 10I:
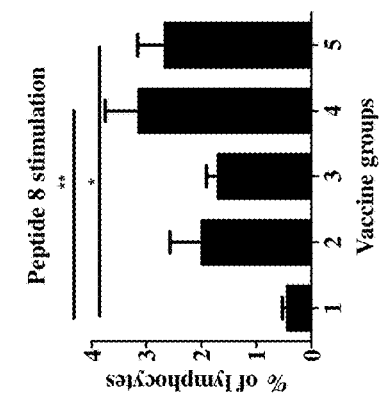
Figure 10J:
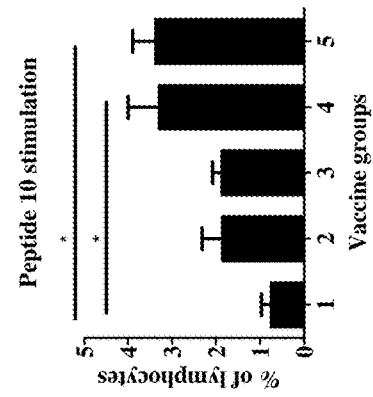
Figure 10K:
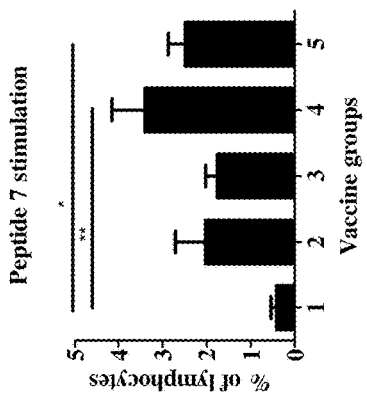
Figure 10L:
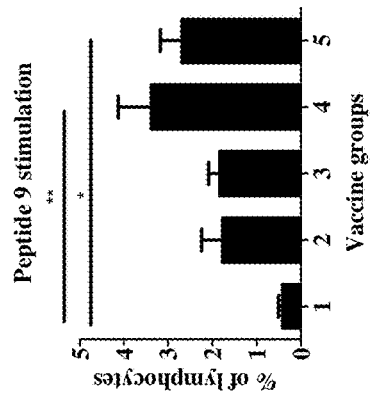
Figure 11A:
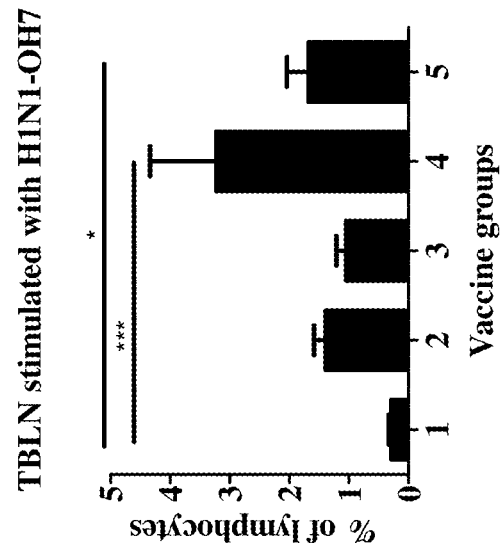
FIGS. 11A and 11B illustrate that virus and peptides epitopes specific T-helper/memory ($CD3^+CD4^+CD8\alpha^+$) cells in TBLNs were significantly increased in the liposome vaccine formulations out of groups 1-5 of Table 5 after restimulation with pooled peptides and H1N1-OH7 virus.
Figure 11B:
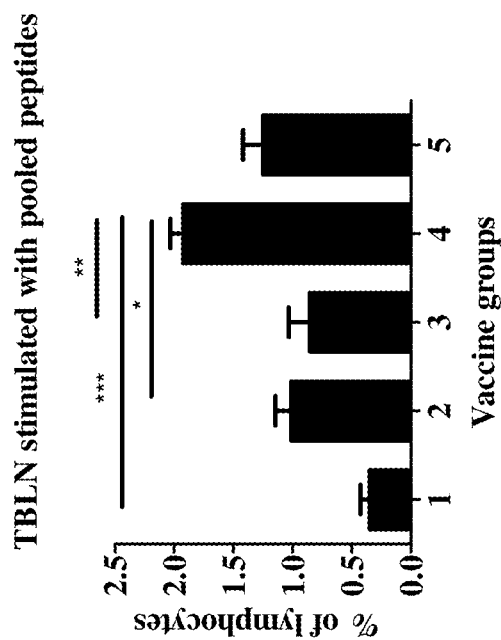

3. Liposomal Vaccine Results in Reduced Virus Shedding in the Nose and Reduced Virus Load in the Bronchioalveolar Lavage (BAL) Fluid:

As shown in FIG. 5 (virus shedding detection in nasal swab samples) and FIG. 6 (virus titer in bronchioalveolar lavage (BAL) fluid at DPC 6, Group 5 (liposome-peptide nanoparticle with SwRI adjuvant) resulted in significant reduction in nasal viral shedding compared to the mock challenge group, and 8 to 16 times reduction in virus titers compared to other vaccine groups. Group 4 and 5 also has the lowest amount of virus titer in BAL fluid. This suggests that the liposomal vaccine induced an immune response against the virus, thus improving against the damage caused by the virus as well as reducing the number of infectious virus particles.

4. Liposomal Vaccine with Adjuvant Formulation Resulted in Better Cytokine Responses:

As shown in FIG. 7A, FIG. 7B, FIG. 7C and FIG. 7D, among all vaccination groups, Group 5 (liposome-peptide nanoparticle with MSU adjuvant) resulted in the lowest amount of IL-6 (an inflammatory marker), while highest amount of IL-10, IL-12 (marker of dendritic cells or macrophage activities), and IFNγ (marker of lymphocyte activity) cytokine.

5. Liposomal Vaccine with Adjuvant Formulation Resulted in Strong Mucosal Immune Response (IgA) Instead of Systemic Immune Response (IgG):

FIGS. 8A through 8F and 9A through 9H illustrate the antibody response utilizing the oligopeptides mixture in Table 2 along with adjuvant delivered in pigs for Groups 1-5 identified in Table 5. The swine influenza virus considered included H1N1-OH7, H1N2-OH10 and H3N2-OH4. HI (hemagglutination inhibition) titers in bronchoalveolar lavage (BAL) fluid showed the highest values for Group 5. IgA response in nasal swab and BAL fluid were also the strongest for Group 5.

6. Liposome Vaccine Formulations Resulted in Strong T-Helper/Memory Cell Response Locally (in TBLN) and Systemically (in Blood):

As shown in FIGS. 10A through 10L and 11A and 11B, with or without adjuvant, liposome formulation resulted in highest number of virus and peptides epitopes specific T-helper/memory cells ($CD3^+CD4^+CD8\alpha^+$) systemically in PBMCs and locally in TBLN mononuclear cells at DPC 6 after restimulation with different peptides or H1N1 virus.

7. Liposome Vaccine (with and without Adjuvant) Produced Strong Antigen-Specific IFN-γ Production by Peripheral Blood Mononuclear Cells (PBMCs), Indicating a Strong Cellular Immune Response:

As shown in FIGS. 12A, 12B, 12C, 12D, 12E, 12F, 12G, 12H, 12I, 12J, 12K and 12L, after vaccination with the liposomal vaccine and the virus challenge, the PBMCs were isolated and cultured in the presence of each different stimulating peptides or peptide pool. The PBMCs responded to the stimulation by producing strong IFN-γ production.

8. Liposome Vaccine (with and without Adjuvant) Resulted in High Proliferative Response of Mononuclear Cells in PBMCs and TBLN after H1N1-OH7 Virus Stimulation.

As illustrated in FIGS. 13A, 13B, 13C and 13D, the liposome vaccines here, without or without adjuvant, indicated a relatively high proliferative response of mononuclear cells in TBLN after pooled oligopeptides and H1N1-OH7 virus stimulation.

9. Relative Expression of T-Bet and GATA3 mRNA in TBLN. T

Figure 14B:
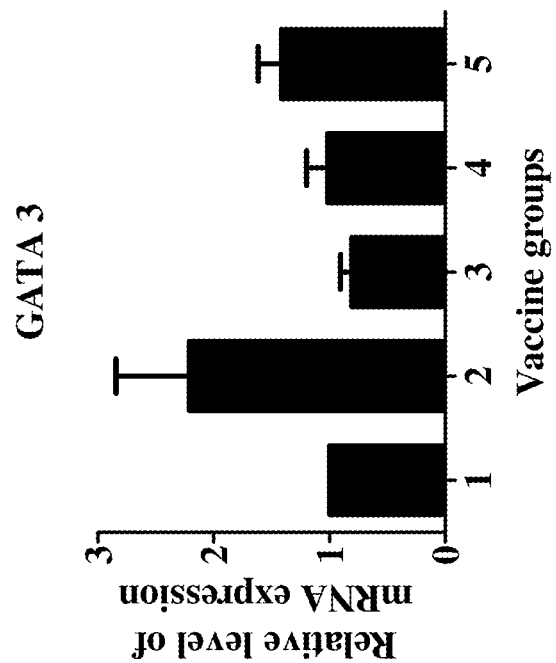
FIGS. 14A and 14B illustrate the relative mRNA expression of transcription factors T-bet and GATA 3, respectively, in groups 1-5 of Table 5.
Figure 14A:
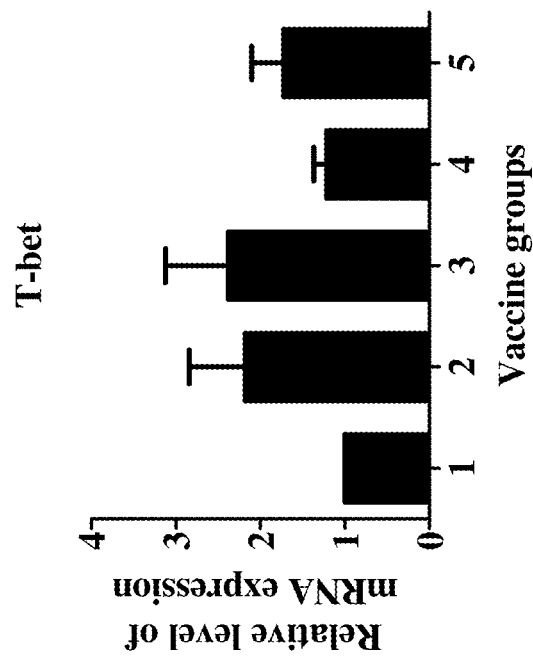

As illustrated in FIGS. 14A and 14B there was no significant difference in expression of T-bet and GATA3 transcription factors which represent T helper type 1 (Th1) and Th2 response, respectively. However, GATA 3 expression was in an increased trend in liposome peptides with adjuvant received group 5 animals.

The invention herein therefore provides use of the oligopeptides or composition as defined above, in the manufacture of a medicament or vaccine, effective in the treatment or prevention of influenza. Also provided is a method of treating or preventing influenza, which method comprises administering the oligopeptides, a composition, a medicament or a vaccine as defined above to a vertebrate. The method of administration is not especially limited, and may comprise subcutaneous, intramuscular, intravenous, intradermal, or intranasal administration, or may be administered orally (e.g. in the form of a pill or a liquid preparation), or may be in the form of a suppository, if desired. For flu vaccination, intranasal administration is preferred. The form of such administration preparations is not especially limited, and known forms may be employed with appropriate modifications that will be apparent to the skilled person. Accordingly, the loaded liposome nanoparticle herein, containing the oligopeptides and optionally the adjuvant and one or more appropriate excipients, serves as a medicament or vaccine composition against influenza.

What is claimed is:

1. An immunogenic composition comprising:
an oligopeptide consisting of the sequence set forth by SEQ ID NO: 1;
an oligopeptide consisting of the sequence set forth by SEQ ID NO: 2;
an oligopeptide consisting of the sequence set forth by SEQ ID NO: 3;
an oligopeptide consisting of the sequence set forth by SEQ ID NO: 4;
an oligopeptide consisting of the sequence set forth by SEQ ID NO: 5;
an oligopeptide consisting of the sequence set forth by SEQ ID NO: 6;
an oligopeptide consisting of the sequence set forth by SEQ ID NO: 7;
an oligopeptide consisting of the sequence set forth by SEQ ID NO: 8;
an oligopeptide consisting of the sequence set forth by SEQ ID NO: 9; and
an oligopeptide consisting of the sequence set forth by SEQ ID NO: 10.

2. The immunogenic composition of claim 1 further comprising an adjuvant.

3. The immunogenic composition of claim 1 wherein said adjuvant comprises mono sodium urate.

4. The immunogenic composition of claim 3 wherein said mono sodium urate is present at a level of 1.0 mg to 10.0 mg.

5. The immunogenic composition of claim 1 contained in a liposome nanoparticle.

6. The immunogenic composition of claim 5 wherein said liposome nanoparticle has a diameter in the range of 50 nm to 200 nm.

7. The immunogenic composition of claim 5 wherein said liposome nanoparticle has a Zeta potential in the range of −15.0 to −25 mV.

8. An immunogenic composition comprising:
an oligopeptide consisting of the sequence set forth by SEQ ID NO: 1;
an oligopeptide consisting of the sequence set forth by SEQ ID NO: 2;
an oligopeptide consisting of the sequence set forth by SEQ ID NO: 3;
an oligopeptide consisting of the sequence set forth by SEQ ID NO: 4;
an oligopeptide consisting of the sequence set forth by SEQ ID NO: 5;
an oligopeptide consisting of the sequence set forth by SEQ ID NO: 6;
an oligopeptide consisting of the sequence set forth by SEQ ID NO: 7;
an oligopeptide consisting of the sequence set forth by SEQ ID NO: 8;
an oligopeptide consisting of the sequence set forth by SEQ ID NO: 9; and
an oligopeptide consisting of the sequence set forth by SEQ ID NO: 10; and
an adjuvant comprising mono sodium urate present at a level of 1.0 mg to 10.0 mg.

9. The immunogenic composition of claim 8 contained in a liposome nanoparticle.

10. The immunogenic composition of claim 9 wherein said liposome nanoparticle has a diameter in the range of 50 nm to 200 nm.

11. The immunogenic composition of claim 9 wherein said liposome nanoparticle has a Zeta potential in the range of −15.0 to −25 mV.

12. A method for eliciting an immune response and conferring protection against influenza virus in a subject, wherein the method comprises administering to the subject a vaccine comprising:
an oligopeptide consisting of the sequence set forth by SEQ ID NO: 1;
an oligopeptide consisting of the sequence set forth by SEQ ID NO: 2;
an oligopeptide consisting of the sequence set forth by SEQ ID NO: 3;
an oligopeptide consisting of the sequence set forth by SEQ ID NO: 4;
an oligopeptide consisting of the sequence set forth by SEQ ID NO: 5;
an oligopeptide consisting of the sequence set forth by SEQ ID NO: 6;
an oligopeptide consisting of the sequence set forth by SEQ ID NO: 7;
an oligopeptide consisting of the sequence set forth by SEQ ID NO: 8;
an oligopeptide consisting of the sequence set forth by SEQ ID NO: 9; and
an oligopeptide consisting of the sequence set forth by SEQ ID NO: 10;
to elicit an immune response and confer protection against influenza virus.

13. The method of claim 12 wherein said vaccine further includes an adjuvant.

14. The method of claim 13 wherein said adjuvant comprises mono sodium urate.

15. The method of claim 14 wherein said mono sodium urate is present at a level of 1.0 mg to 10.0 mg.

16. The method of claim 12 wherein said oligopeptides are contained in a liposome nanoparticle.

17. The method of claim 12 wherein said liposome nanoparticle has a diameter in the range of 50 nm to 200 nm.

18. The method of claim 12 wherein said liposome nanoparticle has a Zeta potential in the range of −15.0 to −25 mV.

19. The method of claim 12 wherein the method of administration is subcutaneous, intramuscular, intravenous, intradermal, intranasal administration, or oral.

* * * * *